United States Patent [19]

Johnson et al.

[11] Patent Number: 5,030,773

[45] Date of Patent: Jul. 9, 1991

[54] PROCESS FOR THE PRODUCTION OF BUTANEDIOL

[75] Inventors: Norman E. Johnson, Pittsfield; Richard T. Miskinis, Lee, both of Mass.; Richard A. Shafer, Mineralwells, W. Va.

[73] Assignee: General Electric Company, Pittsfield, Mass.

[21] Appl. No.: 558,015

[22] Filed: Jul. 25, 1990

[51] Int. Cl.$^5$ .................... C07C 29/136; C07C 31/20
[52] U.S. Cl. .................................................... 568/864
[58] Field of Search ........................................ 568/864

[56] References Cited

U.S. PATENT DOCUMENTS

| | | | |
|---|---|---|---|
| 2,079,414 | 5/1937 | Lazier | 260/156 |
| 4,048,196 | 9/1977 | Broecker et al. | 260/346.11 |
| 4,301,077 | 11/1981 | Pesa et al. | 568/864 |
| 4,405,819 | 9/1983 | Duckwell | 568/864 |
| 4,656,297 | 4/1987 | Kouba et al. | 568/864 |
| 4,751,334 | 6/1988 | Turner et al. | 568/864 |

FOREIGN PATENT DOCUMENTS 2105379  4/1972  France ................. 568/864

*Primary Examiner*—J. E. Evans
*Attorney, Agent, or Firm*—William F. Mufatti; Spencer D. Conard

[57] ABSTRACT

A process for the production of butanediol from the hydrogenation of γ-butyrolactone is provided. The process involves passing vaporized γ-butyrolactone, water and hydrogen over a copper zinc catalyst. The incorporation of water with the γ-butyrolactone and hydrogen results in increased productivity of butanediol.

5 Claims, No Drawings

PROCESS FOR THE PRODUCTION OF BUTANEDIOL

BACKGROUND OF THE INVENTION

1. Field of the Invention

The present invention relates to processes for the production of butanediol, and more particularly relates to the production of butanediol from γ-butyrolactone and hydrogen.

2. Description of Related Art

Broecker et al, U.S. Pat. No. 4,048,196, discloses a three step process for converting maleic anhydride or succinic anhydride to butanediol by (a) hydrogenating maleic anhydride or succinic anhydride in the presence of γ-butyrolactone over a catalyst containing nickel, to give γ-butyrolactone, (b) removing the water formed during the hydrogenation by separating γ-butyrolactone and water from succinic anhydride by distillation, recycling succinic anhydride and separating γ-butyrolactone and water by distillation, and (c) converting γ-butyrolactone into butanediol and/or tetrahydrofuran over a catalyst containing copper and optionally zinc. Note that Broecker teaches the removal of the water from the γ-butyrolactone prior to hydrogenation thereof to butanediol.

SUMMARY OF THE INVENTION

The present invention involves the discovery that by the incorporation of a small weight percentage of water during the hydrogenation of γ-butyrolactone to butanediol, the water improves the productivity of the hydrogenation catalyst. The present process involves the conversion of γ-butyrolactone to butanediol by passing a vaporized mixture of γ-butyrolactone, water and hydrogen over a copper zinc catalyst. The process provides for improved productivity of butanediol.

DETAILED DESCRIPTION OF THE INVENTION

γ-butyrolactone is represented by the formula:

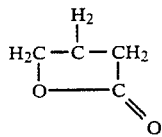

(I)

and may be produced from maleic anhydride or succinic anhydride by hydrogenation. See Broecker et al, U.S. Pat. No. 4,048,196, which is incorporated herein by reference.

The process involves vaporizing γ-butyrolactone and water and admixing therewith hydrogen gas to form a vapor mixture having a mole ratio of hydrogen ($H_2$) to γ-butyrolactone of between 80:1 and 600:1, more preferably between 90:1 and 200:1; and most preferably about 100:1. The water is present in a vapor mixture at a level of from 1% to 6% by weight based on the total weight of γ-butyrolactone and water, more preferably from 2% to 5% by weight thereof, and most preferably about 4% by weight thereof. The vaporized mixture preferably is passed over a copper zinc catalyst at pressures of 600 to 800 psi and temperatures of 180° C. to 210° C. The incorporation of the small amount of water in the mixture provides increased productivity of the catalyst.

A copper catalyst, which also contains zinc hydroxide or zinc oxide, is preferably used. For example, suitable catalysts may be prepared by precipitating, from solutions containing copper and zinc, mixed crystals which crystallographically belong to the malachite type $Cu_2-(OH)_2CO_3$ or the zinc hydroxide/carbonate type $Zn_5(OH)_6(CO_3)_2$, then thermally decomposing these mixed crystals and using the decomposition product, as obtained or after suitable molding, as the catalyst. Such catalysts suitably also contain small amounts of aluminum; the preparation of a suitable catalyst is described, e.g., in German Published Application No. 2,132,020.

EXAMPLES

The following examples illustrate the present invention but are not meant to limit the scope thereof.

| EXAMPLES | | |
|---|---|---|
| | C1 | E2 |
| Feed Material (% GBL/% $H_2O$)[a] | 100/0 | 96/4 |
| Feed Rate (lb/hr) | 7.8 | 8.0 |
| Temp (°C.) | 210 | 210 |
| Pressure (psig) | 600 | 600 |
| $H_2$ Make-up (lb/hr) | 0.5 | 0.50 |
| $H_2$ Recycle (lb/hr) | 17.0 | 17.0 |
| Number of Passes | 1 | 1 |
| Prod (gmol/l-h) | 4.1 | 7.55 |
| $H_2$/GBL (mol ratio) | 93 | 95 |

[a]weight percents
[b]The copper/zinc catalyst used in C1 and E2 was manufactured by United Catalysts, Inc. having the designation C61-3.

Note that the single pass productivity improved substantially for the hydrogenation of γ-butyrolactone to butanediol by the incorporation of a small amount of water along with the hydrogen and γ-butyrolactone.

What is claimed is:

1. A process for the hydrogenation of γ-butyrolactone to butanediol, said process comprising: passing a vaporized mixture of γ-butyrolactone, hydrogen and water over a copper zinc catalyst, said water being present at a level of from 1% to 6% by weight based on the total weight of γ-butyrolactone and water in the vaporized mixture.

2. The process of claim 1 wherein said vaporized mixture is at a temperature of from between 180° C. to 210° C.

3. The process of claim 2 wherein said vaporized mixture is at a pressure of from between 600 and 800 pounds per square inch.

4. The process of claim 1 wherein said hydrogen and γ-butyrolactone are present in said vaporized mixture in a mole ratio of between 80:1 and 600:1.

5. A process for producing butanediol by hydrogenating γ-butyrolactone by passing a vaporized mixture of hydrogen and γ-butyrolactone over a copper catalyst, the improvement comprising: incorporating into said mixture water at a level of from 1% to 6% by weight based on the combined weight of said water and γ-butyrolactone.

* * * * *